(12) United States Patent
Xu et al.

(10) Patent No.: US 8,748,495 B2
(45) Date of Patent: Jun. 10, 2014

(54) METHOD OF PREPARING OIL SUSPENSIONS OF CAROTENOID WITH LOW VISCOSITY AND HIGH FLUIDITY AND USE THEREOF

(75) Inventors: Xinde Xu, Zhejiang Province (CN); Guohua Wei, Zhejiang Province (CN); Xuebing Xiang, Zhejiang Province (CN); Bin Shao, Zhejiang Province (CN)

(73) Assignee: Zhejiang Medicine Co., Ltd. Xinchang Pharmaceutical Factory, Zhejiang Province (CN)

( * ) Notice: Subject to any disclaimer, the term of this patent is extended or adjusted under 35 U.S.C. 154(b) by 25 days.

(21) Appl. No.: 13/255,271

(22) PCT Filed: Mar. 4, 2010

(86) PCT No.: PCT/CN2010/000262
§ 371 (c)(1),
(2), (4) Date: Sep. 8, 2011

(87) PCT Pub. No.: WO2010/102508
PCT Pub. Date: Sep. 16, 2010

(65) Prior Publication Data
US 2012/0329880 A1  Dec. 27, 2012

(30) Foreign Application Priority Data

Mar. 9, 2009  (CN) .......................... 2009 1 0118952

(51) Int. Cl.
*A61K 31/122* (2006.01)

(52) U.S. Cl.
USPC ........................................................ 514/691

(58) Field of Classification Search
None
See application file for complete search history.

(56) References Cited

U.S. PATENT DOCUMENTS

| | | | |
|---|---|---|---|
| 2,918,477 A | 12/1959 | Cattapan et al. | |
| 5,902,890 A * | 5/1999 | Nitsche et al. | 554/174 |
| 6,573,299 B1 | 6/2003 | Petrus | |
| 7,119,238 B2 * | 10/2006 | Khachik | 585/23 |
| 8,097,762 B2 * | 1/2012 | Khachik et al. | 568/825 |
| 2003/0054070 A1 * | 3/2003 | Bridges et al. | 426/73 |
| 2004/0013732 A1 * | 1/2004 | Farber et al. | 424/488 |
| 2004/0022881 A1 | 2/2004 | Hauptmann et al. | |
| 2005/0139145 A1 * | 6/2005 | Quesnel | 117/2 |
| 2008/0194703 A1 * | 8/2008 | Sabio Rey | 514/762 |
| 2010/0144828 A1 | 6/2010 | Wu et al. | |
| 2010/0311827 A1 | 12/2010 | Daneshtalab et al. | |

FOREIGN PATENT DOCUMENTS

| | | |
|---|---|---|
| CN | 1175411 | 3/1998 |
| CN | 1415758 | 5/2003 |
| CN | 1657601 | 8/2005 |
| CN | 101396068 A | 4/2009 |
| EP | 0159180 | 10/1985 |
| EP | 0265071 | 4/1988 |
| EP | 1200462 | 5/2005 |
| JP | 2006 298802 | 11/2006 |
| WO | 98 09964 | 3/1998 |
| WO | 2004 052310 | 6/2004 |
| WO | WO/2005/044769 | * 5/2005 |
| WO | 2005 118585 | 12/2005 |
| WO | 2007 030657 | 3/2007 |
| WO | 2008 098471 | 8/2008 |
| WO | 2009 046618 | 4/2009 |

OTHER PUBLICATIONS

Riggi, E. (Recent Patents on Food, Nutrition & Agriculture, 2010, 2, 75-82).*
Laughlin, R. et al, (Chemistry and Physics of Lipids, 115 (2002), pp. 63-76, where Laughlin et al., teach preparation of beta-carotene with THF (Tetrahydrofuran) for use in Fractional Dissolution (FD purification).*
CDC, "Human Immunodeficiency Virus Type 2," Oct. 1998.
Kashman, et al., "The Calanolides, a Novel HIV-Inhibitory Class of Coumarin Derivatives from the Tropical Rainforest Tree, *Calophyllum lanigerum*," J. Med. Chem. 1992;35, pp. 2735-2743.
Dittmar, et al., "HIV: Epidemiology and Strategies for Therapy and Vaccination," PubMed, Intervirology, 2002;45(4-6), pp. 260-266.
Miles, K. "The Growing HIV Pandemic," PubMed, Community Pract. Aug. 2005;78(8), pp. 292-294.
The Merck Manual, "Human Immunodeficiency Virus (HIV)," pp. 1-16, Accessed Aug. 27, 2009.
The Merck Manual, "Respiratory Viruses," pp. 1-2, Accessed Aug. 27, 2009.

(Continued)

*Primary Examiner* — San-Ming Hui
*Assistant Examiner* — Jeanmarie Calvillo
(74) *Attorney, Agent, or Firm* — Daniel A. Thomson; Emerson Thomson Bennett, LLC

(57) ABSTRACT

The present invention relates to a method for preparing a carotenoid oil suspension with low viscosity and high fluidity. The method includes the steps of mixing carotenoid crystals with tetrahydrofuran, heating the resulting mixture to a reflux temperature of about 50~70° C. under stirring, and filtering the resulting solution to remove fat-soluble fibers. The resulting filtrate is then condensed to dryness, mixed with a ketone solvent, heated to a reflux temperature of about 60~80° C., and filtered to remove non-soluble phospholipids. The filtrate obtained is condensed to a residue, and absolute alcohol is added to the residue, and then crystallized under stirring at room temperature. The resulting crystals are filtered and dried to provide carotenoid crystals. The carotenoid crystals are ground and mixed with plant oils to provide a carotenoid oil suspension with low viscosity and high fluidity, which provides easy filling, for example, into capsules.

24 Claims, No Drawings

(56) References Cited

OTHER PUBLICATIONS

Morissette, et al., "High-Throughput Crystallization: Polymorphs, Salts, co-Crystals and Solvates of Pharmaceutical Solids," Advanced Drug Delivery Reviews 2004, 56, pp. 275-300.

Souillac, et al., "Characterization of Delivery Systems, Differential Scanning Calorimetry," Encyclopedia of Controlled Drug Delivery, 1999, pp. 212-227, John Wiley & Sons.

Vippagunta, et al., "Crystalline Solids," Advanced Drug Delivery Reviews, 2001, 48, pp. 3-26.

Ma, et al., "Synthesis of Chlorogenic Acid Derivatives with Promising Antifungal Activity," Bioorganic & Medicinal Chemistry, 2007, 15, pp. 6830-6833.

The Merck Manual, "Acute Viral Hepatitis," pp. 1-8, Accessed Aug. 27, 2009.

Zhanglihua et al., main formulations of lutein and its use, "China Food Additives", No. 1 2009, pp. 122-125.

* cited by examiner

METHOD OF PREPARING OIL SUSPENSIONS OF CAROTENOID WITH LOW VISCOSITY AND HIGH FLUIDITY AND USE THEREOF

FIELD OF THE INVENTION

The present invention relates to the field of biochemical engineering, in particular, relates to a method of refining carotenoid especially natural carotenoid by a series of physical processes to achieve the purpose of improving the fluidity of oil suspensions.

BACKGROUND OF THE INVENTION

Carotenoids exist widely in nature. Pigment of carbohydrates was firstly crystallized and separated from the carrot roots by Wachenroder in 1831 and named as "carotene". After that, yellow polar pigment are separated and extracted from autumn leaves by Berzelius and named as "xanthophyll". With the development of biophysical technology, a series of natural pigments are separated by chromatographic method and named as "carotenoid". They have common chemical structural characteristics, and their molecular centers are all long chain of polyunsaturated polyisoprene. Many derivatives are produced by the means of cyclization, addition of oxygen or rotation of bond and isomerization. Currently, members of known carotenoids have about more than 600 species.

Carotenoid belongs to terpenoid compounds and is a generic name of two major categories of pigments as carotene and xanthophyl. Carotenoid of hydrocarbon race which molecules have not oxygen atoms are referred to as "carotenes". Derivatives and esters thereof which molecules have oxygenic functional groups, such as hydroxy groups, epoxy groups, methoxyl groups and ketone groups, are referred to as "xanthophylls".

There are hundreds of carotenoids existed in the nature, but there have six species to be common and relatively large amounts, such as β-carotene, astaxanthin, canthaxanthin, lutein, zeaxanthin and lycopene. With the development of biotechnology and synthesis technology, many species of the six carotenoids have many different origins, for example, β-carotene may be obtained by synthesis, and also by fermentation method or cultivating Dunaliella. and also by extracting from natural substances, such as palm oil. Lycopene may be obtained by extracting from tomatoes or fermentation, or also by synthesis. In these carotenoids, lutein is an exception. Currently, because of asymmetrical structure, lutein is only obtained by extracting from plant but not by high cost synthesis method.

These six carotenoids which have similar molecular structures are a kind of hydrocarbons and oxygenated derivatives thereof. They are composed of eight isoprenoid units and only have small differences in a six-member ring at two ends. There are many chromophoric groups with conjugated double bond in the molecular structure of carotenoids, which gives carotenoid a special absorption area (blue light area) in ultraviolet-visible light area. Accordingly, crystal or solution of carotenoid possesses very glorious red. orange or yellow color under visible light. The color varies with different concentration. Carotenoids are deemed as a kind of pigments for a long time. Autumn leaves and all sorts of colorful animals give people incomparable aesthetic feeling in nature. Meanwhile these conjugated double bonds also make carotenoid become a good free radical scavenger which has very strong activity of antioxidant and could effectively block free radical chain reaction in the cells. Thus, carotenoid has many kinds of special and important physiological functions.

β-carotene is the most wide and important carotenoids, and is a favorable provitamin A. According to the amount of Vitamin A in body, β-carotene could automatically decompose to supplement deficiency of Vitamin A. Lutein and zeaxanthin are isomers, and the only difference between them is the different site of a double bond on one of the six-member ring chain-terminating. They are only carotenoids existed in the human eye retina, and they are selectively deposited in the macular region and the whole retina, and their density is the highest around the central fovea of macula and gradually decreased around the retina. These macular pigments are able to effectively prevent from occurrence of oxidation reaction on the retina and have important protective effect on the retina. Lycopene has very good effects on prophylaxis and treatment of prostate disease. Astaxanthin also has important roles of anti-tumor and preventing cancer, etc. This is why lots of epidemiologic studies confirm that consuming fruits and vegetables containing carotenoid usually and regularly decrease the risk of chronic diseases including cardiovascular disease, and meanwhile have beneficial effects on prophylaxis of cancer.

Therefore, nutritionists highly recommend that addition or preventive intake of antioxidant such as vitamin and carotenoid. Food and pharmaceutical market provide consumers a great quantity of the kind of "cell protective agent". Now various health foods added to single or many kinds of carotenoid are presented on the market, but the more effective means to supplement carotenoid for people is to intake in the form of dietary supplement, for example various tablets, hard capsules, soft capsules, etc. Usually only a grain of tablet or capsule can fulfill a day total requirement of carotenoid for one person. Concerning request of these intake way, many kinds of dosage forms of carotenoid are also presented on the market, for example microparticles CarolBeta® and CaroCare® rich in β-carotene suited to tabletting or covering hard capsules, microencapsulation beadlets CarolGold®, FloraGlo®, rich in xanthophyl, microparticle CarolZea® rich in zeaxanthin, microparticle Redivivo® rich in lycopene, etc; And there are some oil suspensions of carotenoid suited to cover soft capsules, but oil suspensions of these carotenoids especially natural carotenoids obtained with natural origins, such as by fermentation method or extracting from plant or algae often exist the following problems: oil suspensions have high fluidity but content of the effective component is low, oil suspensions have high content of carotenoid but have very high viscosity and poor fluidity.

Highly viscous carotenoid oil suspensions are less homogeneous and provide poor fluidity to the suspension, making the suspension undesirable as a filling in soft capsules. Although, heating can reduce the viscosity and increase the fluidity of the oil suspension, the additional step of heating results in an undesirable thermal and chemical degradation of carotenoids.

The main reason for causing oil suspensions poor fluidity is that some fat-soluble fibers and phospholipids are difficult to be removed in the process of carotenoid purification. These small amounts even traces of fat-soluble fibers and phospholipids make viscosity of oil suspensions of carotenoid increase more than ten times even to several hundred times and decrease the fluidity of product. However, there have not been disclosed about method of decreasing or removing small amounts of fat-soluble fibers and phospholipids existed in the natural carotenoid so far.

The present invention tried to decrease or remove the small amounts of fat-soluble fibers and phospholipids existed in carotenoid crystals before preparing for the oil suspension of carotenoid in order to decrease its viscosity and increase its fluidity, further to improve content of carotenoid in oil suspensions.

SUMMARY OF THE INVENTION

The present invention relates to a method of preparing for oil suspensions of carotenoid with low viscosity and high fluidity. By removing residual fat-soluble fibers and phospholipids in the course of preparation for carotenoid crystals as much as possible, the viscosity of oil suspension of carotenoid decreases dramatically. Oil suspensions of carotenoid with low viscosity and high fluidity not only is beneficial to operation and homogenous filling when preparing for soft capsules, but also could improve the content of active ingredients such as carotenoids in oil suspensions, and reduce transport cost and other production cost.

According to one aspect of the present invention, the method of preparing for oil suspensions of carotenoid with low viscosity and high fluidity comprises the following steps:

(1) mixing carotenoid crystals with tetrahydrofuran, heating to reflux temperature 50~70° C. under stirring to dissolve the crystal, filtering to remove fat-soluble fibers, condensing tetrahydrofuran in the mother solution to dryness in vacuum, to obtain the concentrate;

(2) mixing the concentrate with ketone solvent, heating to reflux temperature 60~80° C. to dissolve the mixture, filtering to remove non-soluble phospholipids, condensing ketone solvent in the mother solution to dryness, adding absolute alcohol, crystallizing under stirring at room temperature, filtering and drying in vacuum to obtain carotenoid crystals; and (3) grinding the carotenoid crystals completely and then mix it with plant oils, or mixing the carotenoid crystals with plant oils and then grinding it and then supplementing plant oils, to obtain the oil suspension of carotenoid with low viscosity and high fluidity.

There often exists small amount of fat-soluble fibers and phospholipids in the carotenoid crystals, especially from natural origins (including extracting from plant and producing by fermentation method), without special treatments. These trace impurities have very large influences on the viscosity of oil suspensions of carotenoid. So it is necessary to remove unnecessary fat-soluble fibers and phospholipids as much as possible to improve the fluidity, and the key to remove them is to find a method suitable for industrial production. According to the characteristics of fibers and phospholipids, the present invention removes these impurities conveniently and directly to improve the content of carotenoids, and more importantly, to decrease the viscosity of oil suspensions and improve the fluidity when preparing for corresponding oil suspensions of carotenoid.

In particular, most of impurities such as fat-soluble fibers and phospholipids in the carotenoids are removed by a series of physical processes before preparing for oil suspensions to improve the content of carotenoid crystals.

The carotenoid crystals are treated by purification and re-crystallization, wherein the content of effective component is about 90%.

Firstly, carotenoids especially natural carotenoids, are usually extracted by straight-chain alkanes such as n-hexane and n-butane. dichloromethane, tri-chloromethane, or esters such as ethyl acetate and isobutyl acetate, these solvents often are non-polar or weak polar, but a small amount of fat-soluble fibers could also be extracted in the course of dissolution and extraction. Accordingly, in the following process, organic solvents with stronger polar are used for removing these fat-soluble fibers as much as possible.

In the present invention, organic solvents with strong polarity such as tetrahydrofuran, which has very good solubility to carotenoid but poor solubility to fibers, are selected to remove fat-soluble fibers in the carotenoid crystals.

Secondly, according to physicochemieal property of phospholipids such as insoluble in acetone or butanone while carotenoids soluble in acetone or butanone, carotenoids are dissolved in acetone or butanone. and then a small amount of phospholipids existed in the carotenoid crystals are removed by filtration.

Finally, carotenoid crystals after being removed fat-soluble fibers and phospholipids are converted to micro-powder by a certain micro-smashing measure, then the micro-powder and plant oils arc mixed to obtain the oil suspension of carotenoid with high content and high fluidity, in order to add into the subsequent productions of foods or pharmaceuticals.

According to the present invention, the ratio of tetrahydrofuran in volume (ml) with carotenoid crystals in the original feeding weight (g) is about 5~25: 1 in the step (1); Carotenoid crystals are mixed with tetrahydrofuran, and the mixture is heated up to reflux temperature 50~70° C. under stirring to dissolve the crystals, and the time of dissolution is 0.5~2.0 hr.

According to the present invention, the ratio of ketone solvent in volume (ml) with carotenoid crystals in the original feeding weight (g) is 20~80: 1 in the step (2), and the ketone solvent is acetone or butanone. The concentrate is mixed with ketone solvent, and the mixture is heated up to reflux temperature 60~80° C. to dissolve the concentrate, and the time of dissolution is 0.5~2.0 hr. Condensing ketone solvent in the mother solution to dryness, and then absolute ethanol is added, with the ratio of absolute alcohol in volume (ml) with carotenoid crystals in the original feeding weight (g) is about 0.1~5: 1.

According to the present invention, the plant oil in the step (3) is one or more of sunflower oils, colza oils, corn oils, peanut oils, soybean oils, sesame oils, cottonseed oils, safflower oils, oil-tea camellia seed oils and olive oils; Modes of grinding of carotenoid crystals comprise superfine grinding, ball grinding or jet grinding.

According to the present invention, while the content of carotenoid is 10.0~45.0 wt. % in the oil suspension of carotenoid, the oil suspension of carotenoid has high fluidity at temperature 5~25 □, and meanwhile do not need any extra heating step during applications.

According to the present invention, the carotenoid crystals are β-carotene crystals, astaxanthin crystals, canthaxanthin crystals, lutein crystals, zeaxanthin crystals, or lycopene crystals. The carotenoid crystals are obtained from chemical synthesis, or extracting from plant materials or preparing by fermentation methods. The UV content of the carotenoid crystals is about 50.0%~100.0 wt. % in the step (1), the phosphorus content is about 0.1%~4.5 wt. % in the step (1), the residue on ignition is about 0.01%~3.0 wt. % in the step (1). The UV content of the carotenoid crystals is about 56.1~99.8 wt. % in the step (2), the phosphorus content is about 0.01~1.0 wt. % in the step (2), the residue on ignition is about 0.01~1.0 wt. % in the step (2).

According to another aspect of the present invention, the present invention is to provide uses of oil suspensions of carotenoid with low viscosity and high fluidity in preparing for foods, dietary supplements and pharmaceuticals.

The method of the present invention is described in details as follows: after mixing the carotenoid with 2~25 times of tetrahydrofuran, heating up the mixture to reflux temperature 50~70° C. under stirring, keeping the reflux temperature for 0.5~2 hr, filtering to remove a small amount of fat-soluble fibers and condensing the tetrahydrofuran in the mother solution to dry. 20~80 times amount of ketone solvent such as acetone, butanone, is re-added to the concentrate, heating up the mixture to reflux temperature 50~70° C. to dissolve the concentrate, keeping the reflux temperature for 0.5~2 hr, filtering to remove most of phospholipids and condensing the organic solvent in the mother solution to dry. 0.1~5 times amount of absolute alcohol is added to the above solution, then crystallizing under stirring at room temperature and filtering. Finally, carotenoid crystals are obtained by vacuum dryness. The content of carotenoid in the crystals can be increased by 2~8 percentage than before treatment.

The obtained high content carotenoid crystals are grinded by a proper way, such as superfine grinding, ball grinding, or jet grinding, and then fully mixed with appropriate amount of oils to obtain the oil suspension with required content. The viscosity of the oil suspension is much smaller than untreated crystals corresponding oil suspensions, and the former has high fluidity, thus when filling the soft capsules, it has good maneuverability and do not need any extra heating and dissolution process, in order to avoid the possible content decreasing because of increasing temperature, and the content of effective component between single capsules is uniform.

DETAILED DESCRIPTION AND PREFERRED EMBODIMENTS THEREOF

Hereafter, the present invention will be described specifically with reference to the examples. The examples are given only for illustration of the technical solution of the present invention and should not be construed to limit the present invention.

Example 1

5000 ml tetrahydrofuran is added to 500 g lutein crystals extracted from marigold flower (the UV content: 85.4 wt. %, the phosphorus content: 2.56 wt. %, the residue on ignition: 1.7 wt. %.). The temperature is heated to 65° C. and kept for 0.5 hr under stirring to dissolve the lutein crystals. Then the solution is filtered to obtain a filter cake which is a sticky substance with black brown color, and the weight of the filter cake is 7.53 g after dryness in vacuum.

Condensing tetrahydrofuran in the mother solution to dry, 10.0 L acetone is added to it. The temperature is raised to 60° C. and refluxed for 0.5 hr. Then the above solution is filtered to obtain about 14.3 g phospholipids cream. Condensing the mother solution to dryness, adding 200 ml absolute alcohol, and then filtering the solution to obtain the purified lutein crystals, and the weight of the crystals is about 416 g after dryness in vacuum. The UV content of lutein in the crystals is about 91.3 wt. %, the phosphorus content is about 0.05 wt. %, the residue on ignition is about 0.03 wt. %.

250 g purified lutein crystals and 350 g sunflower oils are mixed and then grinded in a ball-miller. And then 40 g sunflower oils is supplemented to the solution to obtain the oil suspension of lutein, wherein the content of lutein is about 35.7 wt. %. The oil suspension has high fluidity and could flow freely at temperature 5° C.

Example 2

4500 ml tetrahydrofuran is added to 300 g of natural lycopene crystals obtained by fermentation method (the UV content: 50.0 wt. %, the phosphorus content: 3.17 wt. %, the residue on ignition: 3.0 wt. %.). The temperature is raised to 50° C. and kept for 0.2 hr under stirring to dissolve the natural lycopene crystals. Then the solution is filtered to obtain filter cake which is a sticky substance with black brown color, and the weight of the filter cake is 6.47 g after dryness in vacuum.

Condensing tetrahydrofuran in the above mother solution to dryness, 12.0 L acetone is added to it. The temperature is raised to 60° C. and refluxed for 0.5 hr. Then the above solution is filtered to get about 12.4 g phospholipids cream. Condensing the mother solution to dryness, after adding 30 ml absolute alcohol, filtering the solution to obtain the purified natural lycopene crystals, and weight of the crystals is 253.0 g after dryness in vacuum. The UV content of lycopene in the crystals is about 56.1 wt. %, the phosphorus content is about 0.5 wt. %, the residue on ignition is about 0.02 wt. %.

210 g purified lycopene crystals are weighted and after jet grinding, mixed with 968 g corn oils under stirring for 1.0 hr to obtain the oil suspension of lycopene. Wherein the content of lycopene is 10.0 wt. %. The oil suspension has high fluidity and could flow freely at temperature 10° C.

Example 3

2250 ml tetrahydrofuran is added to 450 g natural β-carotene crystals extracted from palm oils (the UV content: 86.7 wt. %, the phosphorus content: 4.5 wt. %, the residue on ignition: 1.6 wt. %.). The temperature is raised to 70° C. and kept for 0.5 hr under stirring for 0.5 hr under stirring to dissolve the natural β-carotene crystals. Then the solution is filtered to obtain filter cake which is a sticky substance with black brown color, and the weight of the filter cake is 8.24 g after dryness in vacuum.

Condensing tetrahydrofuran in the above mother solution to dryness, 9.0 L butanone is added to it. The temperature is raised to 80° C. and refluxed for 2.0 hr. Then the above solution is filtered to get about 24.6 g phospholipids cream. Condensing the mother solution to dryness, the solution is filtered to get purified β-carotene crystals after adding 180 ml absolute alcohol, and the weight of the crystals is 401.0 g after dryness in vacuum. The UV content of β-carotene in the crystals is about 91.5 wt. %, the phosphorus content is about 1.0 wt. %, the residue on ignition is about 0.5 wt. %.

210 g purified β-carotene crystals and 300 g peanut oils are weighted and grinded in a ball-mille for 1.5 hr. And then 120 g peanut oils is supplemented to the solution and stirred homogeneously to obtain β-carotene oil suspension, wherein the content of β-carotene is about 30.5 wt. %. The oil suspension has high fluidity and could flow freely at temperature 25° C.

Example 4

1500 ml tetrahydrofuran is added to 100 g zeaxanthin crystals (obtained from transposition of natural xanthophyl) (the UV content: 90.5 wt. %, the phosphorus content: 1.54 wt. %, the residue on ignition: 2.7 wt. %.). The temperature is raised to 60° C. and kept for 1.0 hr under stirring to dissolve the zeaxanthin crystals. Then the solution is filtered to obtain filter cake which is a sticky substance with black brown color, and the weight of the filter cake is 3.12 g after dryness in vacuum.

Condensing tetrahydrofuran in the above mother solution to dryness. 8.0 L acetone is added to it. The temperature is raised to 60° C. and refluxed for 1.5 hr. Then the above solution is filtered to get about 2.41 g phospholipids cream. Condensing the mother solution to dryness, the solution is filtered to get purified zeaxanthin crystals after adding 500 ml absolute alcohol, and the weight of the crystals are 87.0 g after dryness in vacuum. The UV content of zeaxanthin in the crystals is about 95.8 wt. %, the phosphorus content is about 0.01 wt. %, the residue on ignition is about 1.0 wt. %.

75 g purified zeaxanthin crystals and 150 g colza oils are weighted and grinded in a ball-mille for 1.5 hr. And then 55 g peanut oils is supplemented to the solution and stirred homogeneously to obtain oil suspension of zeaxanthin, wherein the content of β-carotene is 25.7 wt. %. The oil suspension has high fluidity and could flow freely at temperature 5° C.

Example 5

10 L tetrahydrofuran is added to 400 g of astaxanthin crystals obtained from fermentation method (the UV content: 96.4 wt. %, the phosphorus content: 1.87 wt. %. the residue on ignition: 1.8 wt. %.). The temperature is raised to 50° C. and kept for 0.5 hr under stirring to dissolve the astaxanthin crystals. Then the solution is filtered to get filter cake which is a sticky substance with black brown color, and the weight of the filter cake is 8.51 g after dryness in vacuum.

Condensing tetrahydrofuran in the above mother solution to dryness, 15.0 L butanone is added to it. The temperature is raised to 80° C. and re fluxed for 1.0 hr. Then the above solution is filtered to get about 10.2 g phospholipids cream. Condensing the mother solution to dryness, the solution is filtered to get purified natural astaxanthin crystals after adding 100 ml absolute alcohol, and the weight of the crystals are 359.0 g after dryness in vacuum. The UV content of astaxanthin in the crystals is about 99.2 wt. %, the phosphorus content is about 0.01 wt. %, the residue on ignition is about 0.08 wt. %.

300 g purified astaxanthin crystals are weighted and superfine grinded, and then mixed with 620 g mixture oils containing corn oils and sunflower oils (2:1) under stirring for 1.0 hr to obtain the oil suspension of astaxanthin. Wherein the content of astaxanthin is 32.6 wt. %. The oil suspension has high fluidity and could flow freely at temperature 10° C.

Example 6

13.75 L tetrahydrofuran is added to 550 g canthaxanthin crystals obtained from total chemical synthesis (the UV content: 100.0 wt. %, the phosphorus content: 0.1 wt. %, the residue on ignition: 0.01 wt. %.). The temperature is raised to 50° C. and kept for 1.0 hr under stirring to dissolve the canthaxanthin crystals. Then the solution is filtered to get filter cake which is a sticky substance with black brown color, and the weight of the filter cake is 2.51 g after dryness in vacuum.

Condensing tetrahydrofuran in the above mother solution to dryness, 20.0 L butanone is added to it. The temperature is raised to 80° C. and refluxed for 1.0 hr. Then the above solution is filtered to get about 4.2 g phospholipids cream. Condensing the mother solution to dryness, the solution is filtered to get purified natural canthaxanthin crystals after adding 300 ml absolute alcohol, and the weight of the crystals are 539.0 g after dryness in vacuum. The UV content of canthaxanthin in the crystals is about 99.8 wt. %, the phosphorus content is about 0.06 wt. %, the residue on ignition is about 0.01 wt. %.

200 g purified canthaxanthin crystals are weighted and superfine grinded, and then mixed with 244 g mixture oils containing safflower oils and sesame oils (1:1) under stirring for about 1.0 hr to obtain the oil suspension of canthaxanthin. Wherein the content of canthaxanthin is 45.0 wt. %. The oil suspension has high fluidity and could flow freely at temperature 15° C.

Example 7

(Comparative Example 1)

150 g purified zeaxanthin crystals in the example 4 and 410 g colza oils are mixed and grinded in a ball-mille for 1.5 hr. And the mixture has no fluidity at all at temperature 25° C. with the content of zeaxanthin in the mixture is 24.2 wt. %. Then colza oils are supplemented to the solution to 384.0 g of the supplementing amount. This mixture begins to have high fluidity at temperature 25° C., and the content of zeaxanthin in the oil suspension is 14.3 wt. %.

Example 8

(Comparative Example 2)

8.0 L acetone is directly added to 100 g purified zeaxanthin crystals in the Example 4 which is not treated by tetrahydrofuran. The temperature is raised to 60° C. and refluxed for 1.5 hr. Then the above solution is filtered to get about 3.27 g phospholipids cream. Condensing the mother solution to dryness, the solution is filtered to get purified zeaxanthin crystals after adding 50 ml absolute alcohol, and the weight of the crystals are 91.0 g after dryness in vacuum. The UV content of zeaxanthin in the crystals is about 93.6 wt. %, the phosphorus content is about 0.01 wt. %, the residue on ignition is about 1.8 wt %.

75 g purified zeaxanthin crystals and 150 g colza oils are mixed and grinded in a ball-mille for 1.5 hr. And then 55 g peanut oils is supplemented to the solution and stirred homogeneously to obtain oil suspension of zeaxanthin, wherein the content of zeaxanthin is 25.7 wt. %. When the oil suspension is heated up to 40° C., it has no fluidity yet. Then 114 g colza oils are continuously supplemented to the solution under stirring and the oil suspension begins to have fluidity at temperature 25° C. The content of zeaxanthin in the oil suspension is 17.8 wt. %.

The comparative result of Table 1 is obtained from the above-mentioned Examples 1~6 and Examples 7 and 8 using the prior art.

TABLE 1

Fluidity of Oil Suspensions of Carotenoid

| Example | Carotenoids | Content of Carotenoid (wt. %) | Fluidity of Oil Suspensions |
|---|---|---|---|
| 1 | Lutein | 35.7 | It can flow freely at temperature 5° C. |
| 2 | Lycopene | 10.0 | It can flow freely at temperature 10° C. |
| 3 | β-Carotene | 30.5 | It can flow freely at temperature 25° C. |
| 4 | Zeaxanthin | 25.7 | It can flow freely at temperature 5° C. |
| 5 | Astaxanthin | 32.6 | It can flow freely at temperature 10° C. |
| 6 | Canthaxanthin | 45.0 | It can flow freely at temperature 15° C. |
| 7 | Zeaxanthin | 24.2 | There is no flow phenomenon at temperature 25° C. |
|  |  | 14.3 | There is not a flow phenomenon till at temperature 25° C. |

TABLE 1-continued

Fluidity of Oil Suspensions of Carotenoid

| Example | Carotenoids | Content of Carotenoid (wt. %) | Fluidity of Oil Suspensions |
|---|---|---|---|
| 8 | Zeaxanthin | 25.7 | There is no flow phenomenon at temperature 40° C. |
| | | 17.8 | There is not a flow phenomenon till at temperature 25° C. |

It can be seen from comparing Example 7 (the Comparative Example 1) of the prior art 1 with Example 4 of the present invention that when zeaxanthin crystals are pretreated by using the method of the present invention, the content of the oil suspension of the present invention can increase from 14,3 wt. % of the prior art to 25.7 wt. % of the present invention under the condition of keeping high fluidity. And the oil suspension of the prior art has fluidity till at temperature 25° C., however the oil suspension of the present invention has better fluidity at temperature 5° C.

It can be seen from comparing Example 8 (Comparative Example 2) of the prior art 2 with Example 4 of the present invention that when zeaxanthin crystals are pretreated by using the method of the present invention, the content of the oil suspension of the present invention can increase from 17.8 wt. % of the prior art to 25.7 wt. % of the present invention, under the condition of keeping high fluidity. And the oil suspension of the prior art has fluidity till at temperature 25° C., however the oil suspension of the present invention has better fluidity at temperature 5° C.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A method of preparing carotenoid oil suspensions having a low viscosity and a high fluidity, comprising the following steps:
   (1) mixing carotenoid crystals with tetrahydrofuran (THF), heating the mixture to a reflux temperature 50~70° C. under stirring to dissolve the crystals, filtering the resulting solution to remove fat-soluble fibers and obtain a first filtrate comprising the THF, condensing the first filtrate to dryness under vacuum to remove the THF to obtain a concentrate,
   wherein the carotenoid crystals are characterized as having about 50-100 wt. % of carotene;
   (2) mixing the concentrate with a ketone solvent, heating the mixture to a reflux temperature of 60~80° C. to dissolve the concentrate, filtering the resulting solution to remove non-soluble phospholipids and obtain a second filtrate comprising the ketone solvent, condensing the second filtrate to dryness to remove the ketone to obtain a residue, adding absolute alcohol to the residue and crystallizing the residue under stirring at room temperature, filtering and drying the resulting crystals under vacuum to obtain carotenoid crystals; and
   (3) grinding the carotenoid crystals and mixing the ground crystals with plant oils to obtain an oil mixture, or mixing the carotenoid crystals with plant oils and grinding the resulting oil mixture and then adding plant oils to the resulting oil mixture to obtain the carotenoid oil suspension with a low viscosity and a high fluidity.

2. The method according to claim 1, wherein the ratio of tetrahydrofuran in volume (ml) with carotenoid crystals in the original feeding weight (g) is 5~25:1 in step (1).

3. The method according to claim 1, wherein the time of dissolution is 0.5~2.0 hr in step (1).

4. The method according to claim 1, wherein the ratio of ketone solvent in volume (ml) with carotenoid crystals in the original feeding weight (g) is 20~80:1 in step (2).

5. The method according to claim 1, wherein the time of dissolution of the concentrate in the ketone solvent in step (2) is 0.5~2.0 hr.

6. The method according to claim 1, wherein the ketone solvent is acetone or butanone in step (2).

7. The method according to claim 1, wherein the ratio of absolute alcohol in volume (ml) with carotenoid crystals in the original feeding weight (g) is 0.5~5:1.

8. The method according to claim 1, wherein the plant oil described in step (3) is one or more of sunflower oils, cozola oils, corn oils, peanut oils, soybean oils, sesame oils, cottonseed oils, safflower oils, oil-tea camellia seed oils and olive oils.

9. The method according to claim 1, wherein the modes of grinding of carotenoid crystals in step (3) comprise superfine grinding, ball grinding or jet grinding.

10. The method according to claim 1, wherein the resulting carotenoid oil suspension has a content of carotenoid of about 10.0~45.0 wt. %, the oil suspension has a high fluidity at a temperature of 5~25° C. whereby the oil suspension does not need any heating during the application of being filled into a capsule.

11. The method according to claim 1, wherein the carotenoid crystals are chosen from the group comprising: β-carotene crystals, astaxanthin crystals, canthaxanthin crystals, lutein crystals, zeaxanthin crystals, and lycopene crystals.

12. The method according to claim 11, wherein the carotenoid crystals are obtained by chemical synthesis, or extracting from plant material, or preparing by fermentation methods.

13. The method according to claim 12, wherein the UV content of the carotenoid crystals is about 50.0~100.0 wt. % in step (1), phosphorus content is about 0.1%~4.50 wt. % in step (1), and the content of residue on ignition is about 0.01%~3.0 wt. % in step (1).

14. The method according to claim 12, wherein the UV content of the carotenoid crystals is about 56.1~99.8 wt. % in step (2), phosphorus content is about 0.01%~1.0 wt. % in step (2), and the content of residue on ignition is about 0.01%~1.0 wt. % in step (2).

15. A food, dietary supplement, or a pharmaceutical made according to the method of claim 1.

16. A method for preparing a carotenoid oil suspension having a low viscosity and a high fluidity, the method comprising:
   (1) mixing carotenoid crystals with tetrahydrofuran (THF), heating the mixture to a reflux temperature of about 50-70° C. under stirring to dissolve the crystals, filtering the resulting solution to remove fat-soluble fibers, and condensing the filtrate to dryness under vacuum to remove the THF and obtain a concentrate, wherein the ratio of the volume (ml) of THF and the original feeding weight of carotenoid crystals is about 5-25:1, and wherein the carotenoid crystals are characterized by UV as having about 50-100 wt. % of carotene, a phosphorus content of about 0.1~4.5 wt. % and a content of residue on ignition of about 0.01-3.0 wt. %;

(2) mixing the concentrate with a ketone solvent, heating the mixture to a reflux temperature of about 60-80° C. to dissolve the concentrate, filtering the resulting solution to remove non-soluble phospholipids, condensing the filtrate to dryness to remove the ketone and obtain a residue, adding absolute alcohol to the residue and crystallizing the residue under stirring at room temperature, filtering and drying the resulting crystals in vacuum to obtain carotenoid crystals, wherein the ratio of the volume (ml) of ketone solvent and the original feeding weight of carotenoid crystals is about 20-80:1, the ketone solvent is acetone or butanone, the ratio of the volume (ml) of absolute alcohol and the original feeding weight of carotenoid crystals is about 0.1-5:1, and wherein the obtained carotenoid crystals are characterized by UV as having about 56.1-99.8 wt. %, the phosphorus content is about 0.01-1.0 wt. %, and the content of residue on ignition is about 0.01-1.0 wt. %;

(3) grinding the obtained carotenoid crystals and mixing the ground crystals with plant oils to obtain a carotenoid oil suspension, or mixing the carotenoid crystals with plant oils and grinding the resulting oil mixture to obtain a carotenoid oil suspension, wherein the resulting carotenoid oil suspension has a low viscosity and a high fluidity.

17. The method according to claim 16, wherein the time of dissolution is 0.5~2.0 hr in step (1).

18. The method according to claim 16, wherein the time of dissolution of the concentrate in the ketone solvent in step (2) is 0.5~2.0 hr.

19. The method according to claim 16, wherein the plant oil is one or more of sunflower oil, cozola oil, corn oil, peanut oil, soybean oil, sesame oil, cottonseed oil, safflower oil, oil-tea camellia seed oil and olive oil.

20. The method according to claim 16, wherein the mode of grinding of carotenoid crystals in step (3) comprises superfine grinding, ball grinding and jet grinding.

21. The method according to claim 16, wherein the resulting carotenoid oil suspension has a content of carotenoid of about 10.0~45.0 wt. %, a high fluidity at a temperature of 5~25° C. whereby the oil suspension does not need any heating during the application of being filled into a capsule.

22. The method according to claim 16, wherein the carotenoid crystals comprise one or more of β-carotene crystals, astaxanthin crystals, canthaxanthin crystals, lutein crystals, zeaxanthin crystals, and lycopene crystals.

23. The method according to claim 22, wherein the carotenoid crystals are obtained by one or more of chemical synthesis, extraction from a plant material, or chemical fermentation.

24. A food, dietary supplement, or a pharmaceutical made according to the method of claim 16.

* * * * *